United States Patent
Peplinski

[11] Patent Number: 5,810,794
[45] Date of Patent: Sep. 22, 1998

[54] EYE DROP DISPENSING DEVICE

[76] Inventor: Lee S. Peplinski, 611 Wardshire Pl., Louisville, Ky. 40223

[21] Appl. No.: 752,572

[22] Filed: Nov. 21, 1996

[51] Int. Cl.$^6$ .................................................. A61M 35/00
[52] U.S. Cl. ........................................... 604/295; 604/300
[58] Field of Search ..................................... 222/214, 420, 222/421, 422; 604/294, 295, 298, 299, 300, 301, 302

[56] References Cited

U.S. PATENT DOCUMENTS

| | | | |
|---|---|---|---|
| 282,986 | 8/1883 | Higgins | 222/214 |
| 473,516 | 4/1892 | Maranville | 222/214 |
| 3,934,590 | 1/1976 | Campagna et al. | 128/233 |
| 4,085,750 | 4/1978 | Bosshold | 128/233 |
| 4,543,096 | 9/1985 | Keene | 604/300 |
| 4,685,906 | 8/1987 | Murphy | 604/300 |
| 4,733,802 | 3/1988 | Sheldon | 222/181 |
| 4,792,334 | 12/1988 | Py | 604/295 |
| 4,834,727 | 5/1989 | Cope | 604/300 |
| 4,960,407 | 10/1990 | Cope | 604/300 |
| 4,981,479 | 1/1991 | Py | 604/302 |
| 5,007,905 | 4/1991 | Bauer | 604/295 |
| 5,261,571 | 11/1993 | Goncalves | 222/214 |

FOREIGN PATENT DOCUMENTS

| | | |
|---|---|---|
| 594860 | 3/1934 | Germany. |

*Primary Examiner*—John G. Weiss
*Assistant Examiner*—David J. Cho

[57] ABSTRACT

An improved eye drop dispensing device for use with conventional eyedropper bottles comprising a ring-shaped base to fit within the orbital area of the eye and engage the eye lids and correctly position the dropper bottle over the eye, connected to a retention collar for gripping the eye dropper bottle such that the opening within the collar to receive said bottle enlarges when squeezed via contralateral connections to the device frame and narrows when released allowing the collar to resiliently grip the dropper bottle, with adjustable arm-shaped members to straddle the dropper bottle reservoir and aid in releasing an eye drop onto the eye when squeezed together.

5 Claims, 5 Drawing Sheets

EYE DROP DISPENSING DEVICE

BACKGROUND-FIELD OF INVENTION

This invention relates to devices designed to facilitate the administration of ophthalmic solution in droplet form from a conventional eye dropper bottle onto a recipient eye.

BACKGROUND-DESCRIPTION OF PRIOR ART

Liquid medications for the eye are widely used and commonly available in eye drop form. These eye drops are typically packaged in soft-sided squeeze dropper bottles of various shapes and sizes, each having a nozzle through which the drops are discharged and may then fall upon a recipient's eye. Several problems may be encountered when attempting to use such a dropper bottle. Accuracy of drop placement is difficult when self-administering, when vision is not sufficient to allow for proper alignment, or when placing into a non-cooperative recipient. This can not only waste medication, but also render damage to an eye through inadequate dosage of the medication. Reflex eye lid closure during drop administration also can prevent the drop from contacting the eye. Since such dropper bottles are supported solely by the users hand, accidental contact between the dropper bottle and the eye can occur, resulting in both injury and contamination of the medication and/or the eye. Poor hand control or dexterity from arthritis, Parkinson's disease, or other medical conditions can affect not only alignment and the separation of the dropper bottle and eye, but also the ability to apply pressure to the bottle to cause release of the eye drop.

Numerous eye drop dispenser attachments and systems have been proposed over the years to address these problems. Typically, such prior art eye drop dispensing devices still rely excessively on eye-hand coordination and require two hands to operate. Other prior art devices affix to the dropper bottle in a manner that would preclude its use with a variety of bottle types and sizes (different screw thread patterns, etc.). Further, some of these prior art devices include various types of elongate leg members which could inadvertently poke into a eye and cause harm. In general, no such prior art exists that addresses each of these above problems concurrently.

SUMMARY AND OBJECTS OF THE INVENTION

In accordance with the invention, the foregoing advantages have been achieved through the present eye drop dispensing system for dispensing eye drops from a conventional dropper bottle onto a recipient eye, overcoming the shortcomings of the prior art devices. The preferred embodiment of the present invention comprises: A frame for support and alignment of a standard eye dropper bottle; a means of attaching said frame to said bottle in such a manner to be easily and quickly achieved on a variety of bottle shapes and sizes; and a means for aiding and squeezing said bottle to release the eye drop medication.

A feature of the present invention resides in the fact that the base frame is ring-shaped and sized to fit within the orbital area of the eye. Thus, the base will rest on the eye lids of the recipient eye and help to overcome any blink reflex associated with eye drop placement.

Another feature of the present invention resides in the fact that the means for attachment to the eye dropper bottle includes a collar, in two parts, for securing around the neck of the bottle. Each portion of the collar is semi-circular in shape and mounted to the contralateral aspect of the superior portion of the frame, which in turn is attached to the base ring. Materials used should be flexible but resilient, so as to open the collar for reception of a bottle neck when the superior portion of the frame is squeezed together, but return to form, allowing the collar to secure the bottle neck when the superior portion of the frame is released. Thus, different bottles may be easily interchanged if more than one medication is to be used, even if the user has poor dexterity.

Another feature of the present invention resides in the fact that the superior portion of the frame along with the collar is spaced properly from the base ring so as to direct the nozzle tip of the bottle to the proper height and position over the eye to prevent contact with and contamination from/of the eye.

A further feature of the present invention involves (two) vertical poles extending up from the frame, one from each half of the superior portion of the frame, but in the same tangential plane relative to the collar, with wings that can extend anteriorly from the poles, one from either pole. The wings are adjustable in height, may have a convex shape relative to the space between them and may have finger pads at their distal ends to facilitate gripping. Upon placement of a dropper bottle in the retention collar, the wings are adjusted along the vertical poles and set to "straddle" the center of the reservoir of the dropper bottle. When squeezing the finger pads or wings together, a lever action applies force to the dropper bottle reservoir releasing a dose of medication from the dropper nozzle of the bottle into the eye. At the same time an outward counter-force is applied to the vertical poles which secures the dropper bottle in the retention collar.

Accordingly, the object of the present art is an eye drop dispensing device which:

(1) Aids in accurately aligning a dropper bottle and in squeezing the dropper bottle to release an eye drop onto the eye;

(2) Can be easily and quickly attached to most eye dropper bottles;

(3) Can be easily used by patients having poor vision and/or poor dexterity or may be used single-handedly;

(4) Supports the dropper bottle so as to prevent contact with the eye;

(5) Helps maintain open eye lids during drop placement;

(6) And is simple and economical to manufacture, clean, and use.

Other objects, features, or advantages and a fuller understanding of the invention will become apparent from the following description of the presently preferred embodiment of the same taken in connection with the accompanying drawings.

DRAWING FIGURES

Figure 1:
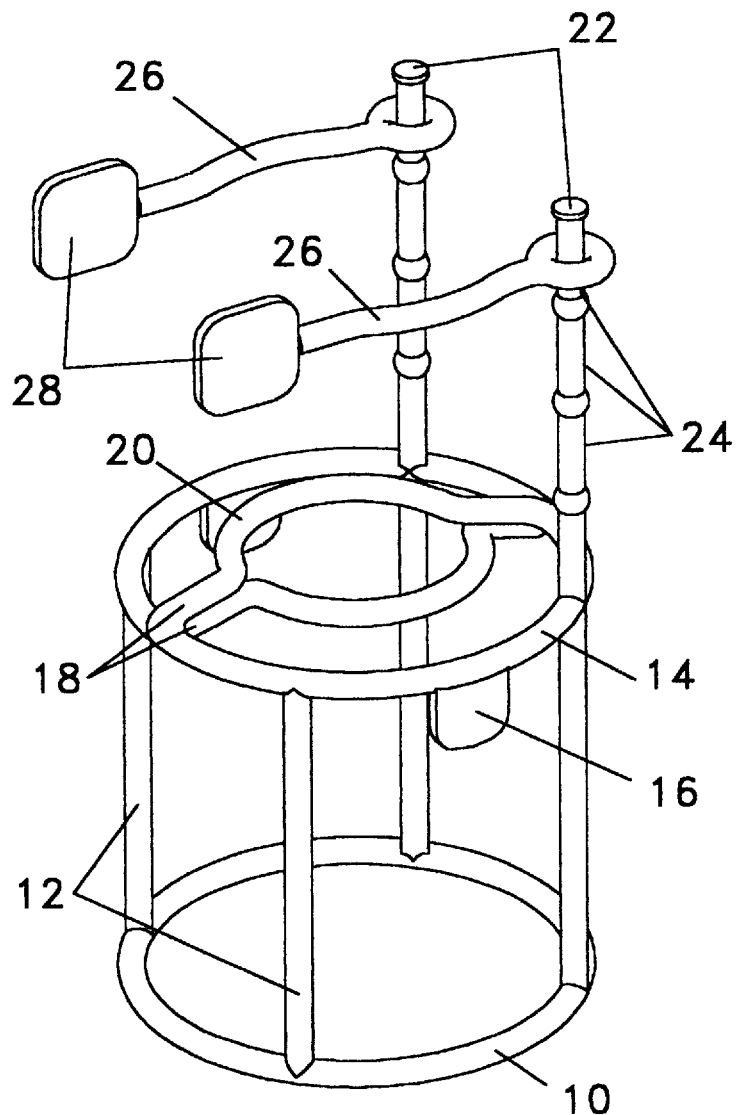
FIG. 1 is a prospective view of the preferred embodiment of the present invention.
Figure 2:
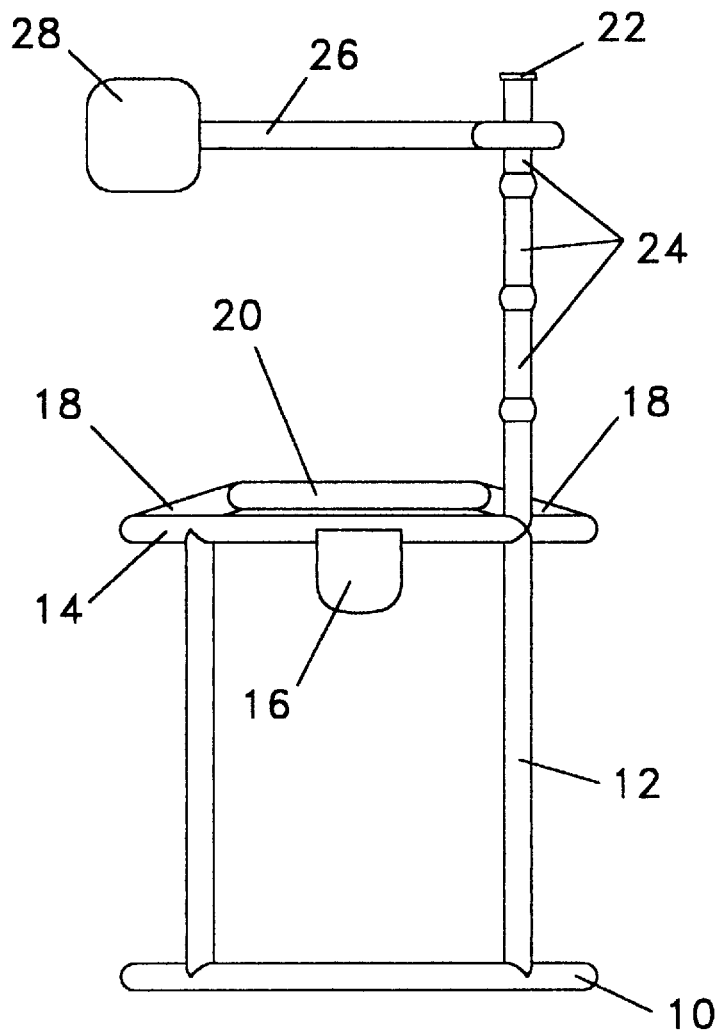
FIG. 2 is a side view of the same.

The invention will be described in connection with the preferred embodiment, and it will be understood that it is not intended to limit the invention to that embodiment. On the contrary, it is intended to cover all alternatives, modifications, and equivalents as may be included within the spirit and scope of the invention and defined by the appended claims.

REFERENCE NUMERALS IN DRAWINGS

| 10 base frame | 12 support posts |
|---|---|
| 14 superior frame | 16 finger holds |
| 18 connectors | 20 retention collar |
| 22 vertical poles | 24 notches |
| 26 pincer wings | 28 finger pads |
| 30 dropper bottle | 32 bottle neck |
| 34 bottle tip | 36 opening |

DESCRIPTION OF THE INVENTION

Figure 3:
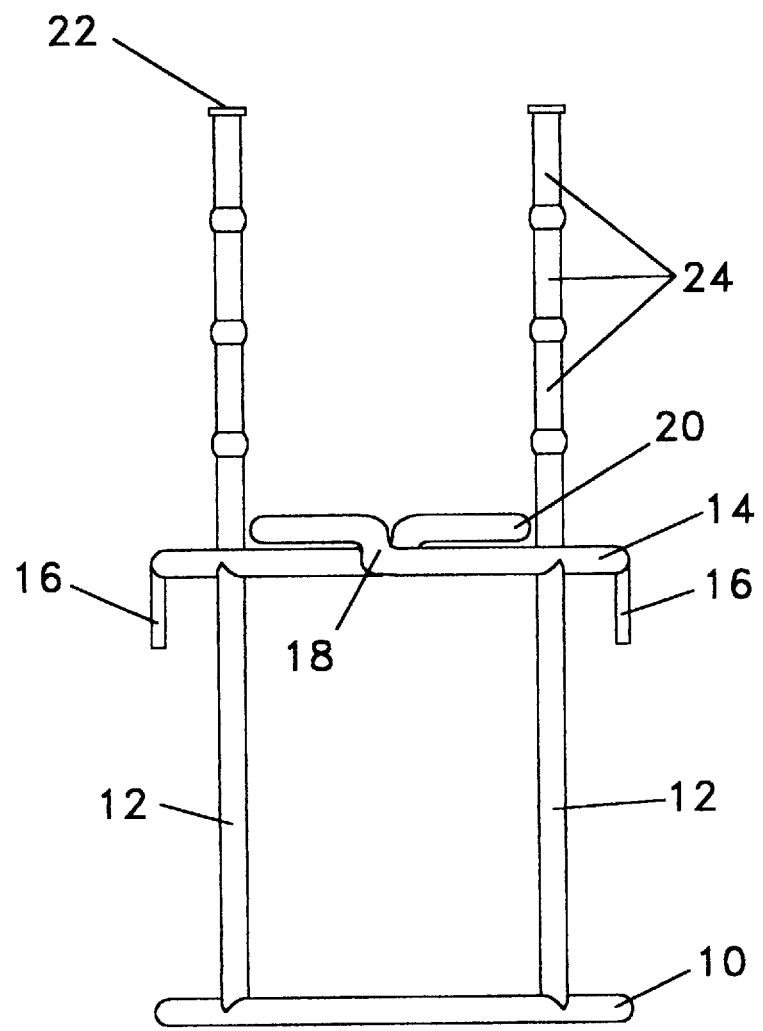
FIG. 3 is an end view thereof, viewed in a direction perpendicular to the view of FIG. 2.

The embodiment of the present invention shown in FIGS. 1 through 6 is an eye drop dispensing device made of a flexible material which can maintain its resilience. The base frame 10 is preferably ring-shaped to fit within the orbital area of the eye, but may also be oval or oblong shaped. Extending vertically from the base frame 10 are four support posts 12 connecting to the superior frame 14. In the preferred embodiment, the superior frame 14 is split into two halves, each connecting to two adjacent support posts 12, each having the same curvature as the base frame 10, but each in a separate plane relative to the base frame 10 (FIG. 3). Finger holds 16 may be located on the superior frame 14 equidistant between the support posts 12 to facilitate gripping the device.

Figure 5:
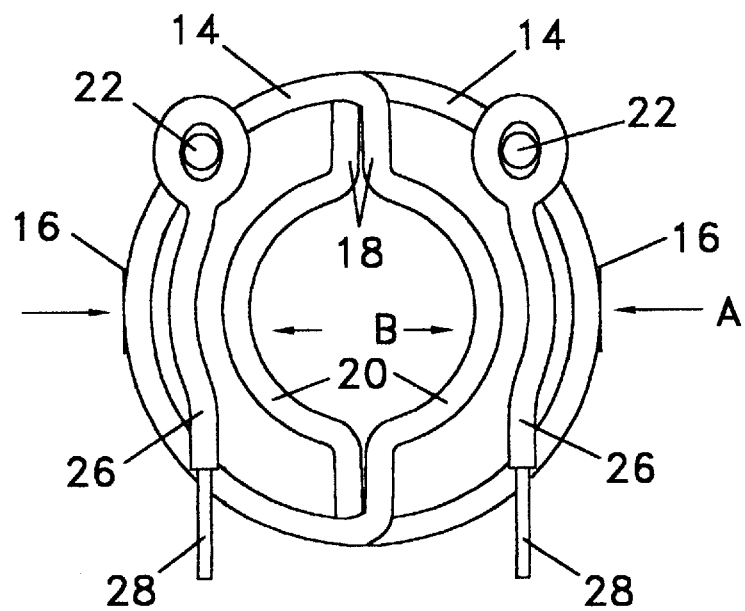
FIG. 5 is a plan view of the device.
Figure 6:
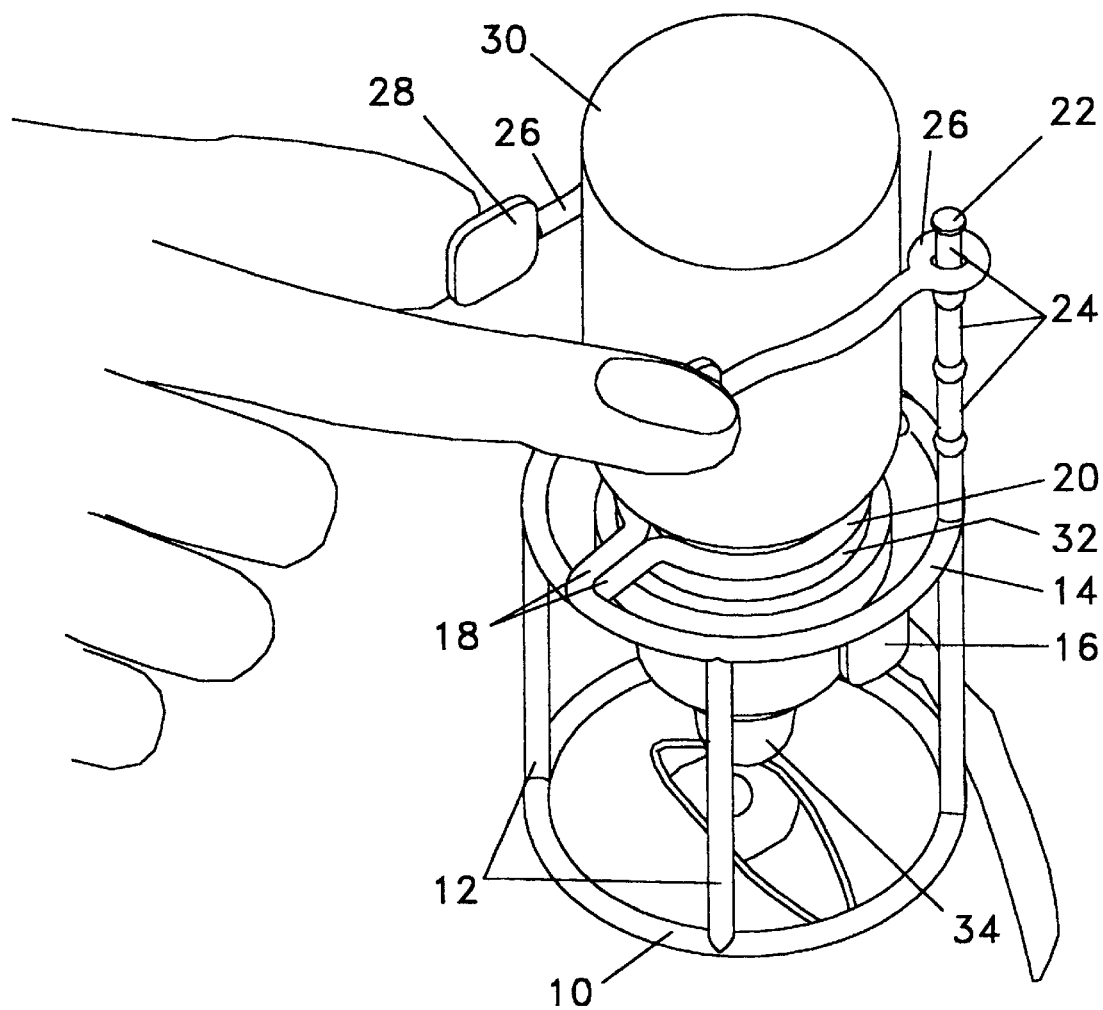
FIG. 6 is a prospective view, on a reduced scale, showing the present invention in use.

Extending from the distal ends of each half of the superior frame 14 are connectors 18 to the retention collar 20. The retention collar 20 is likewise in two halves, but each attached to the contralateral superior frame 14. Each half of the retention collar 20 is in the same plane relative to the base frame 10 due to the orientation of the connectors 18 (see FIGS. 1, 2, and 3). Each half of the retention collar 20 is semi-circular in shape but of a smaller radius of curvature than the superior frame 14 and base frame 10 (FIGS. 1 and 5).

Figure 4:
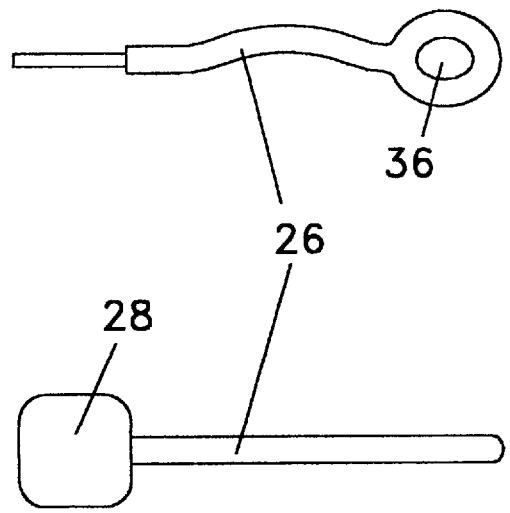
FIG. 4 is a plan and side view of the pincer wing.

A vertical pole 22 extends above the superior frame 14 from two adjacent support posts 12, one connected to each half of the superior frame 14. A pincer wing 26 attaches to each vertical pole 22 and extends parallel to the plane of the retention collar 20. One pincer wing 26 will reach around each side of dropper bottle 30 (FIG. 6) when said bottle is placed in the device. In the preferred embodiment, the pincer wings 26 are adjustable in height to fit various size dropper bottles 30, the vertical poles 22 being notched 24 accordingly. FIG. 4 shows each pincer wing 26 has an oval (or ring-shaped) opening 36 to fit around a vertical pole 22. The shaft of the pincer wing 26 may be straight, or bowed to better grasp a dropper bottle 30. The distal end of each pincer wings 26 has a finger pad 28 to facilitate proper gripping when in use.

Operations

When the present invention illustrated in FIGS. 1 through 6 is used, the dropper bottle 30 is first secured in said invention by means of the retention collar 20 securing about the neck 32 of the dropper bottle 30. This is accomplished by grasping the finger holds 16 with the thumb and index finger of one hand and squeezing them gently together (along line A, FIG. 5). This, in turn, separates the two halves of the retention collar 20 (B, FIG. 5) to allow insertion of the dropper and tip 34 to the point where the bottle neck 32 can be clamped by the retention collar 20. Releasing the finger holds 16 allows the natural resilience of the support post 12 to return the retention collar 20 to its original position, now secured about the neck 32 of the dropper bottle 30. Next, the pincer wings 26 are adjusted up and down the vertical poles 22 and secured in the appropriate notch 24 to obtain the optimal position about the reservoir on the dropper bottle 30.

With the body reclined or the head tilted back to a chin-up position, the device with dropper bottle (FIG. 6) is then placed over the recipient eye. The base frame 10 is placed within the orbital area of the eye so that it rests on the eye lids, helping to keep the eye lids open and overcome any blink reflex. The ring shape of the base frame 10 allows the user to use whichever directional orientation is most comfortable. The device automatically places the tip of the dropper bottle 30 at the appropriate location relative to the eye (FIG. 6) and does not allow contact between the eye and the dropper bottle 30. The finger pads 28 are then gently squeezed together, applying force through the pincer wings 26 to the dropper bottle 30 causing release of a drop from the dropper tip 34 onto the users eye. This action also results in a lever action, applying outward force on the vertical poles 22 (C, FIG. 6), thus tightening the retention collar 20 about the neck 32 of the dropper bottle 30 and further securing it in place. This can all be done with one hand if finger and thumb are positioned on the finger pads 28 prior to positioning the device with dropper bottle over the recipient eye.

After removal from the eye, grasping the finger holds 16 and squeezing then opens the retention collar 20, allowing for removal of the dropper bottle 30 and fast and easy replacement with another (if needed).

Ramifications and Scope

From the above, it will be appreciated, that several novel advantages are enjoyed by the present invention. This invention:

(a) Not only aligns the dropper bottle before the eye but also aids in squeezing the bottle for release of an eye drop onto the eye;

(b) Can be more easily and quickly attached than prior art to most eye dropper bottles and will accommodate and fit more bottle styles and sizes;

(c) Is easily used by and of great benefit for users with poor vision or poor dexterity, may be used and attached single handedly, and allows for the most comfortable orientation of the device;

(d) Prevents the dropper bottle from contacting the eye and thus contaminating the dropper bottle or injuring or infecting the eye;

(e) Helps maintain open eye lids during drop placement and minimizes inadvertent blinking, thus improving compliance and minimizing waste; and (f) Is simple and economical to manufacture, clean, and use.

Although the present invention has been described with reference to particular embodiments, herein set forth, it is understood that the present disclosure has been made only by way of example and that numerous changes in the details of construction may be resorted to without departing from the spirit and scope of the invention. For example, the base frame 10 may be oval or other shape; the support posts 12 may extend at an acute angle from the base frame 10 and connect directly to the contralateral retention collar 20; each half of the retention collar 20 may have a hyperbolic (rather than semi-circular) shape to better adapt and fit to different sized bottle necks 32; pincer wings 26 may have other means of attaching to the vertical poles 22 or adjusting thereon so as to better fit the dropper bottle 30; both pincer wings 26 may extend from the same single vertical pole 22; etc. Thus, it is intended that the scope of the invention not be limited by the foregoing specification but rather only by the scope of the appended claims and their legal equivalents.

I claim:

1. An eye drop dispensing device which facilitates the release of an eye drop from a conventional eye dropper bottle attached to said device and which supports and aligns said bottle before the recipient eye, said device comprising:

wing means for straddling the conventional eye dropper bottle reservoir and squeezing said reservoir when pinched together, and further including finger pads on said wing means;

attachment means for connecting said wing means to said device;

said device connecting to said dropper bottle by two are portions of a predetermined curvature which securely clamps between the arc portion a bottle's neck located between said bottle reservoir and a bottle tip;

said arc portions mounted on separate post means extending down a predetermined distance and connecting to a generally circular base ring such that each arc portion connects to said base ring under the opposite arc portion;

said arc portions generally in proximal relation to each other but separate when said post means are squeezed together and return to the proximal relationship when said post means are released;

said base ring sized to fit over the eye of a recipient within eye's orbital area and engage eye lids of said eye when said device is used.

2. The device of claim 1 further including finger holds connected to said post means and said arc portions.

3. An eye drop dispensing device which attaches to a conventional eye dropper bottles to support and align an eye dropper bottle and facilitate the release of an eye drop from said bottle, said device comprising:

a generally circular ring sized to fit over the eye of a recipient within eye's orbital area;

post means extending upwardly from said ring;

arcuate means mounted on said post means a predetermined distance form said ring;

said arcuate means comprises a pair of arcs in proximal relation to each other, each arc portion being mounted on an upper end of separate post means which attach to said ring under the opposite arc portion so as to separate said arc portions when said post means are squeezed together and allow said arc portions to return to the proximal relationship when said post means are released;

said arc portions are of a predetermined curvature to securely clamp between the arc portions of a conventional eye dropper bottle's neck located between said bottles reservoir and the bottle tip when in the proximal position;

wing means for straddling said dropper bottle's reservoir when said dropper bottle is placed in said device to aid in squeezing said dropper bottle reservoir when pinched together.

4. The device of claim 3 further including finger holds connected to said post means and said arc portions.

5. A method for instilling eye drops from a conventional eye dropper bottle onto a recipient eye, comprising the steps of:

securing said dropper bottle to a support device comprised of a base for support and alignment of a standard eye dropper bottle, a means of attaching said base to said bottle in such a manner to be easily and quickly achieved, and a wing means for straddling said dropper bottle's reservoir to aid in squeezing said dropper bottle reservoir when pinched together to release the eye drop medication;

positioning a recipient into a prone or head-back position so that the recipient eye is looking generally upward;

placing the base of said device with said dropper bottle attached within recipient eye's orbital area onto the eye lids on said recipient;

gently squeezing said wing means until a drop is forced from said bottle onto recipient eye;

removing said device and said dropper from said eye.

\* \* \* \* \*